United States Patent [19]

Anderson et al.

[11] Patent Number: 5,270,164
[45] Date of Patent: Dec. 14, 1993

[54] PROCESS FOR ENHANCING THE CHEMILUMINESCENCE OF ENZYME-TRIGGERED 1,2-DIOXETANES AND USES THEREFOR

[75] Inventors: Lynne E. Anderson; Robert K. Kobos, both of Wilmington, Del.; Shay E. Polsky, West Chester, Pa.

[73] Assignee: E. I. Du Pont de Nemours and Company, Wilmington, Del.

[21] Appl. No.: 24,700

[22] Filed: Mar. 1, 1993

Related U.S. Application Data

[63] Continuation of Ser. No. 738,408, Jul. 31, 1991, abandoned.

[51] Int. Cl.⁵ .............. C12Q 1/68; G01N 33/535
[52] U.S. Cl. .............................. 435/6; 435/7.72; 435/7.9; 435/7.92; 435/21; 435/968; 436/518
[58] Field of Search ........ 435/6, 7.72, 7.9, 7.92, 435/21, 968; 436/518, 531, 546, 529, 530

[56] References Cited

U.S. PATENT DOCUMENTS

| | | | |
|---|---|---|---|
| 4,705,847 | 11/1987 | Hummelen et al. | 530/350 |
| 4,857,652 | 8/1989 | Schaap | 549/510 |
| 4,948,975 | 8/1990 | Erwin et al. | 250/361 |
| 4,952,707 | 8/1990 | Edwards et al. | 549/221 |
| 4,956,477 | 9/1990 | Bronstein et al. | 549/221 |
| 4,959,182 | 9/1990 | Schaap | 252/700 |
| 5,089,423 | 2/1993 | Diamandis et al. | 436/518 |

FOREIGN PATENT DOCUMENTS

| | | |
|---|---|---|
| 8936340 | 12/1989 | Australia . |
| 0261719 | 3/1988 | European Pat. Off. . |
| 8603840 | 7/1986 | PCT Int'l Appl. . |
| 8800695 | 1/1988 | PCT Int'l Appl. . |
| 8906650 | 7/1989 | PCT Int'l Appl. . |

OTHER PUBLICATIONS

Schaop et al Tetrahedron Letters 78 #11 pp. 1159–1162 (1987).
Wood J. Clin. Chem. Clin. Biochem. 38 pp. 481–483 (1990).
Pollard-Knight et al. Anal. Biochem. 185 pp. 353–358 (1990).
Beck & Koster, Analytical Chemistry, vol. 62, No. 21, Nov. 1, 1990.
Bronstein et al., J. Biolumin, Chemilumin. 4, 99–111 (1989).
J. C. Hummelen et al., Methods in Enzymology, vol. 133, pp. 531–557 (1986).
Kiel, Bioelectromagnetics 4, 193–204 (1983).
Southern Light Protocol.
Photogene Nucleic Acid Detection System.
Willard, Merritt, Dean and Settle, *Methods of Analysis*, Sixth Edition, D. Van Nostrand & Co., 1981 pp. 111–113.
A. K. Campbell, *Chemiluminescence: Principles and Applications in Biology and Medicine, Eliis Horwood Publishing Co., 1988, pp. 81–87.*

Primary Examiner—Esther L. Kepplinger
Assistant Examiner—Lora Marie Green

[57] ABSTRACT

A process is disclosed for the enhancement of the chemiluminescence of enzyme-triggered 1,2-dioxetanes detectable within a sample. The process comprises first providing a solid support having sample disposed thereon and suitably treated with a solution including enzyme-triggered 1,2-dioxetanes. The solid support is next dried and optionally heated either simultaneously with drying or thereafter. The steps of drying and/or heating are conducted either prior to or simultaneously with detection.

18 Claims, 2 Drawing Sheets

PROCESS FOR ENHANCING THE CHEMILUMINESCENCE OF ENZYME-TRIGGERED 1,2-DIOXETANES AND USES THEREFOR

This is a continuation of application Ser. No. 07/738,408, filed Jul. 31, 1991 now abandoned.

FIELD OF THE INVENTION

The present invention relates to a process for enhancing the chemiluminescent signals generated by enzymatic triggering of certain substituted 1,2-dioxetanes. More particularly, the present invention relates to drying alone or in combination with heating membranes or other hydrophobic solid supports which contain a suspect sample and which have been prepared for chemiluminescent activity, resulting in enhanced chemiluminescent intensity.

BACKGROUND OF THE INVENTION

Chemiluminescent compounds are those which undergo a chemical reaction resulting in the emission of light energy, referred to as luminescence. In such reactions, the product of the chemical reaction is in an electronically excited state capable of undergoing a radiative transition to a ground state with the accompanying emission of radiant energy. The chemiluminescence of dioxetanes when enzyme-triggered is useful in, for example, the field of immunoassay. If the reaction is carried out in solution, the light emission lasts approximately 1-2 minutes. If the reaction is carried out in conjunction with a sample affixed to a membrane or other solid support, the dioxetane intermediate responsible for the light emission has increased stability, resulting in a light emission lasting as much as several days.

Chemiluminescent signals via enzymatic triggering of certain substituted 1,2 dioxetanes have been reported by several groups. In general, such references teach the generation and use of chemiluminescent signals produced by enzymatic cleavage of a labile group from a substituted 1,2-dioxetane. Following the removal of the enzyme-cleavable group, an intermediate anion is formed, which subsequently decomposes by rupture of the dioxetane ring. At least one of the resulting carbonyl compounds formed is a light-emitting fluorophore.

U.S. Pat. No. 4,857,652 to Schapp discloses light producing 1,2-dioxetanes of the formula

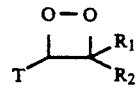

wherein ArOX is an aryl ring substituted with an X oxy group and A are passive organic groups which allow the 1,2-dioxetane to produce light when triggered by removing X. X is a chemically labile group which is removed by an activating agent. The 1,2-dioxetane compounds can be triggered to produce light at room temperatures.

U.S. Pat. No. 4,952,707 to Edwards et al., affords a general description of enzymatically-cleavable 1,2-dioxetanes. This patent describes enzymatically-cleavable chemiluminescent 1,2-dioxetanes having the formula:

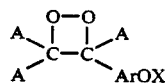

wherein $R_1$ is hydrogen, or a bond when $R_2$ is a substituent bound to the dioxetane ring through a spiro linkage, or an organic substituent that does not interfere with the production of light; $R_2$ is a fused polycyclic ring-containing fluorophore moiety having an enzymatically-cleavable, labile ring substituent; and T is a stabilizing group that prevents the dioxetane compound from decomposing before the enzymatically-cleavable labile ring substituent's bond is cleaved.

U.S. Pat. No. 4,956,477 to Bronstein et al., also describes the synthesis of enzyme-cleavable 1,2-dioxetanes, useful for chemiluminescent immunoassays, DNA probe assays, and direct assays for an enzyme.

U.S. Pat. No. 4,959,182 to Schaap describes a method and composition for providing enhanced chemiluminescence from 1,2-dioxetanes. In this method an enzyme cleavable 1,2-dioxetane is mixed with a surfactant and a fluorescent compound attached to a hydrocarbon to form a co-surfactant in a micelle or other structure. This method provides an enhancement of 500 fold in signal for enzyme-triggered chemiluminescence of 1,2-dioxetanes in solution. Moreover, Bronstein et al., (J. Biolumin. Chemilumin. 4, 99-111, 1989) report that bovine serum albumin and other water-soluble macromolecules provide a significant enhancement of chemiluminescent signal generated from enzyme-cleavable 1,2-dioxetanes in solution. All of these enhancers are believed to increase the stability of the anion intermediate and the light-emitting species by keeping them in a hydrophobic environment. However, on a hydrophobic support such as a nylon membrane, the support provides a hydrophobic environment for the anionic species. Consequently, no significant enhancement is provided by these enhancers when the enzyme is immobilized on a hydrophobic support.

AU-A36340/89 to Okada et al. describes a method for enhancing the chemiluminescent signal from enzyme-triggered 1,2-dioxetanes. The enzymatic reaction is performed at the optimum pH for the enzyme. Afterwards the pH is increased by the addition of strong base to enhance the luminescent reaction. Increases in signal from 7 to 59 fold were reported for assays done on polystyrene beads. This method does not produce as large an enhancement as our heat-drying during detection method and requires the use of a caustic chemical, 1 N NaOH.

WO89/06650 to Bronstein et al. discusses dioxetanes for use in assays, and including a fluorescent chromophore spiro-bound at the 4-carbon of the dioxetane. The dioxetane has the formula:

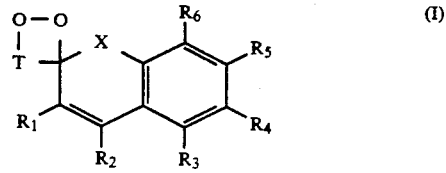

where X is $CR_6R_8$, O, S, or R—R (where each $R_7$, $R_8$, and R, independently, is H, alkyl, heteroalkyl, aryl, heteroaryl, cycloalkyl, cycloheteroalkyl, aralkyl, aklaryl, or an enzyme cleavable group). Each $R_1$, $R_2$, $R_3$, $R_4$, $R_5$, and $R_6$, independently, is H, an electron withdrawing group, an electron donating group, heteroaryl, or an enzyme cleavable group, or groups $R_1$-$R_6$ together form a ring. T is a substituted or unsubstituted aryl, polyaryl, cycloalkylidene or polycycloaklylidene group spiro-bound at the 3-carbon of the dioxetane. These dioxetanes are used in an assay to detect a member of a specific binding pair or an enzyme.

U.S. Pat. No. 4,705,847 to Hummelen et al. relates to a process for preparing substituted polycyclo-alkylidene polycyclo-alkanes, such as substituted adamantylidene adamantanes, and the corresponding epidioxy compounds. The polycycloalkylidene polycycloalkanes are halogenated, and thereafter the halogenation product is optionally subjected to a substitution reaction. The resulting products are converted to the corresponding epidioxy compounds. Various epodioxy compounds are disclosed which contain a dioxetane ring. These compounds are useful as thermochemiluminescent labels.

The use of 1,2-dioxetanes as labels for thermochemiluminescent immunoassays is reviewed by J. C. Hummelen et al. in Methods in Enzymology, Vol. 133, pp. 531-557, 1986. When heated, the 1,2-dioxetanes decompose thermally into two carbonyl fragments. A fraction of these fragments are formed in an electronically excited state and emit radiant energy upon transition to the ground state. In a thermochemiluminescent binding assay, one binding partner is labeled with the 1,2-dioxetane. After the binding reaction between the labeled partner and the immobilized partner, the support is heated to 150° C. to 250° C. to generate the chemiluminescent signal.

The main distinction between this approach and the instant invention is the use of enzyme-triggered 1,2-dioxetanes. The enzyme is used as the label, and the dioxetane is the substrate. The intermediate that is formed by the enzymatic reaction is thermally triggered to produce enhanced chemiluminescence. Basically, the present approach is a combination of enzyme generated chemiluminescence and thermochemiluminescence. There are two major advantages to the present approach. The sensitivity is greater because of enzyme amplification, i.e., the enzymatic reaction can be allowed to proceed until sufficient intermediate is formed. The second advantage is that lower temperatures are used because the intermediate is not as stable as the thermochemiluminescent dioxetanes used as labels. High stability is not required for the intermediate, as it is in the case of thermochemiluminescent labels, because the intermediate is formed in situ by the enzymatic reaction.

U.S. Pat. No. 4,948,975 to Erwin et al., describes a quantitative luminescence imaging system which provides a means to measure low light levels from luminescent reactions in electromagnetic fields, e.g., microwave radiation, and its use in the areas of chemiluminescent assays and thermal microdosimetry. The effect of the microwave radiation on chemiluminescence described in the patent and in a publication (Kiel, Bioelectromagnetics 4,193-204, 1983) is significantly different from the instant description. The system described involves enzymatic reactions, specifically the oxidation of luminol catalyzed by peroxidase enzymes, in protein gels which are kept wet with solution. The enhancement affected by microwave radiation is due to an increased mobility of substrate (hydrogen peroxide) within the gel, not to an actual enhancement of the chemiluminescent process as presently disclosed.

These and other references broadly describe chemiluminescent processes involving dioxetanes. However, none of the references describe a method to enhance the chemiluminescent signal of enzyme triggered 1,2-dioxetanes on solid supports using drying or a combination of drying and heating the support.

Therefore, it is an object of the present invention to provide a process for enhancing the chemiluminescent signal produced by enzyme-triggered 1,2-dioxetanes. It is a further object of this invention to enhance signal intensity in solid phase assays over a reduced time period and without labor intensive procedures or equipment. A feature of the present invention is that the chemiluminescent signals of the enzyme-triggered 1,2-dioxetanes are increased 4-6 fold employing the drying techniques disclosed herein (and fully 100 fold when the heating step disclosed herein is additionally utilized), over signal strengths detected using conventional techniques in which the membrane is kept wet with substrate solution. An advantage of the present process is its versatility in several applications including solid phase assays such as enzyme linked immunosorbent assays (ELISAs) and DNA probe assays. Further the enhancement is useful for imaging nucleic acid or protein blots where a camera apparatus is used; the present procedure features the capability to capture images quickly and at great intensity, avoiding concerns such as camera cooling and background noise levels.

These and other objects, features, and advantages of the present invention will become more readily appreciated and understood upon having reference to the following description of the invention herein.

SUMMARY OF THE INVENTION

The present invention is directed to a process for the enhancement of chemiluminescence of enzyme-triggered 1,2-dioxetanes detectable within a sample. The process comprises:

a) providing a solid support having sample disposed thereon and suitably treated with a solution including enzyme-triggered 1,2-dioxetanes;

b) drying said solid support; and c) optionally heating said solid support simultaneously with drying or thereafter;

said drying and/or heating being conducted either prior to or simultaneously with detection of the chemiluminescent signal.

DETAILED DESCRIPTION OF THE INVENTION

Figure 1:
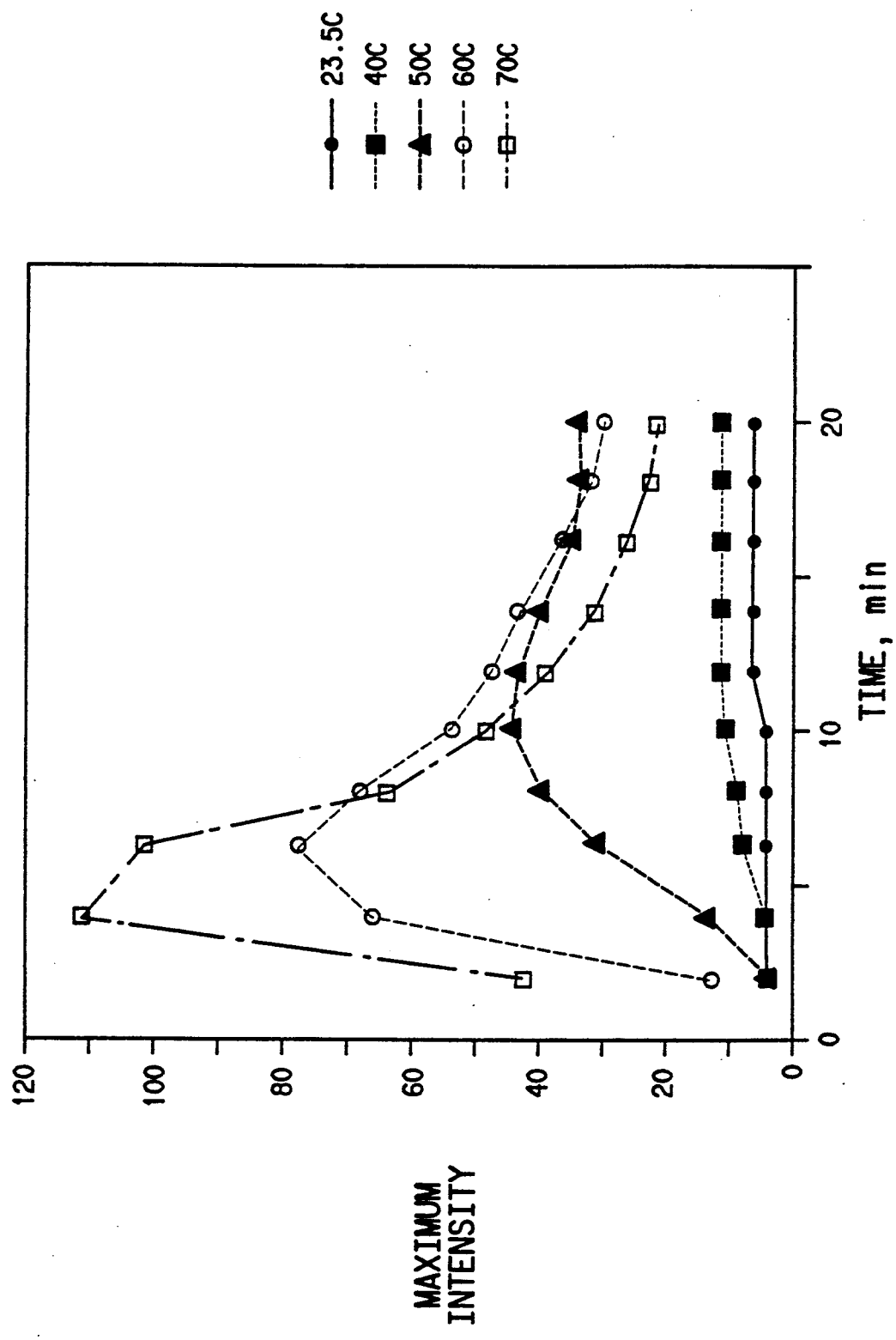
FIGS. 1 and 2 illustrate the effect of temperature on chemiluminescence for the embodiment of Example 7 herein.

The present invention characterizes the effect of drying and heating a solid support on the chemiluminescent response. An important aspect of the invention is the discovery that drying and heating when used together have enhancement characteristics superior to drying alone. Heating has a beneficial effect only with a dry membrane or one that is dried at the same time it is heated. Heating a membrane that is kept wet by sealing it in a bag containing substrate solution results in a lower signal.

Drying the membrane before detection, regardless of the method used, produces a 4-6 fold improvement in signal. Heat-drying in an oven gave the most consistent results, but a similar effect was observed with vacuum drying, air drying, or drying with a heat lamp. The additional effect of heating occurs when the membrane is heated during the capture of the image with, for example, a CCD camera, i.e., the membrane is heated while the picture is being taken. A dry membrane or a wet membrane can be heated during the capture of the image because the membrane dries very quickly when heated directly on a heating block. The employment of these steps is a new concept in enzyme-triggered chemiluminescence. The enhancement that is observed is obtained when carbonate buffer is used as the assay buffer. Much lower signals are obtained when one of the other common buffers for alkaline phosphatase assays, e.g., Tris, diethanolamine, and 2-amino-2-methyl-1-propanol, are used as the assay buffer.

This is contrary to other work in this field, which suggests a deleterious effect of heating and drying components used in an enzymatic process, on chemiluminescent properties. In fact, published protocols for the use of enzyme-activated 1,2-dioxetane substrates for DNA detection on membranes state that the membrane should not be allowed to dry before or during the detection step (Tropix Southern-Light (tm) Protocol). Further the recommended procedure to date is to seal the moist membrane, after incubation in substrate solution, in a plastic bag (Tropix Southern-Light (tm) Protocol) or a plastic folder (BRL PhotoGene (tm) Instruction Manual) for detection.

Several combinations of drying with or without subsequent heating the sample are claimed herein. Each variation on the process of the invention should be reviewed against the particular need of the researcher. Thus, drying the sample prior to detection but heating the sample during detection, and heat-drying simultaneously during detection are preferred procedures when practical. In some cases where heating during detection is not practical, e.g., detection using X-ray or photographic film, heat-drying prior to detection is a preferred approach.

Other useful combinations of heating and/or drying (and their relationship to the detection step) include drying the sample alone (without further heating once the sample is dry) prior to detection; drying the sample and then in sequence heating the sample, both prior to detection; drying the sample alone during detection (although not practical given the time involved and not favored as the signal remains constant for some time after the membrane is dry); and drying and heating the sample simultaneously with detection.

By "drying" the solid support containing the sample it is meant that residual solvent or other aqueous solution is removed from the sample. Without intending to be bound by any particular theory, one possible explanation for the beneficial effects of drying in the process that has been advanced is that the sample (typically a membrane) is free of solvent molecules that can collide with the excited molecules, so that less energy is lost to collision dissipation resulting in an increase in quantum efficiency. Solvent molecules are removed by drying, which eliminates collisional quenching of the chemiluminescence. Drying the membrane before detection results in a 4-fold to 6-fold increase in signal strength over conventional techniques in which the membrane is kept wet with substrate solution. The membrane must be completely dry to realize the full enhancement effect.

In the drying step of the process, the solid support is introduced for a suitable time and temperature to a procedure selected from the group consisting of vacuum drying, convection drying, air drying, the use of microwave energy, and the use of electrical energy. Thus, when drying by vacuum system about 15 to 30 minutes at ambient temperature is sufficient. Convection drying (using for example conventional ovens) is accomplished in about 5-30 minutes at 30°-100° C. air drying is concluded in 30 minutes or longer (several hours) duration at ambient temperature. Drying depends on a number of parameters, e.g., the size of the membrane, the composition of the membrane, and the initial wetness of the membrane. The drying conditions will need to be optimized for every application. The conditions that are given were developed for nylon membranes, $8 \times 8$ cm in size or smaller that are blotted before drying to remove excess solution.

For drying the membrane, the selection of drying method is governed by convenience. The only requirement is that the membrane is thoroughly dried. A preferred procedure is electrical heating of wet or previously dried membranes during detection with a CCD camera. The optimum conditions will depend on the application. For some applications, producing the highest signal in the shortest time interval may be desirable. This would require using a high temperature, e.g., 100° C. It may be desirable to have a more sustained emission using a lower temperature, e.g., 70°-80° C., so that multiple exposures of varying length can be taken. In this way, higher concentration lanes are read at shorter exposures, while lower concentration lanes are read at longer exposures. This approach increases the dynamic range of the system.

By "heating" the sample it is meant that after the removal of solution from the sample, heat or other energy is applied to the sample to raise the temperature therein. Without again intending to be bound by any particular theory, one possible explanation for the beneficial effects of heating in the process that has been advanced is that heating appears to decompose the intermediate molecules quicker and/or more completely, resulting in a more intense signal gathered over a much shorter time as opposed to conventional techniques not applying heat measures. In the process, heating is accomplished by introducing the solid support for a suitable time and temperature to any of a variety of procedures, such as electrical heating, infrared radiation (e.g., heat lamp) heating, convective heating, and microwave heating. Typical procedures used in conjunction with microwave heating require that the membrane be dried in an incubator or convection oven at 30° C. for 30-45 minutes. Then the membrane is placed in a conventional microwave oven (750 watts) for 20-30 seconds. Other forms of drying and/or heating can be used as follows:

In electrical heating during detection with a previously dried membrane, the membrane is dried in a convection oven for 10-30 minutes at 40° C. Then the membrane is placed on an electrically heated plate and heated at 40°-100° C. for 30 seconds to 10 minutes while the signal is measured using a CCD camera. A series of images is taken, typically 30 seconds to 2 minutes, and the image that gives the best signal to background ratio is selected.

A heat lamp may be used to heat-dry membranes prior to detection. The wet membrane is placed on a sheet of blotter paper and dried under the heat lamp (375 watt bulb) for 5-20 minutes. Detection is done with X-ray film or a CCD camera.

For heat-drying during detection, a wet membrane is placed on an electrically heated plate under a CCD camera. The membrane is heat-dried at 40°-100° C. for 30 seconds to 10 minutes. A series of images is taken with the CCD camera, typically 30 seconds to 2 minutes, and the image that gives the best signal to background ratio is selected.

It is further suggested that it should be possible to heat membranes during detection using microwave radiation, although this procedure was not attempted.

Heating is typically conducted for 1-10 minutes at 40°-100° C. Heating may also be viewed as one way to dry the membrane. There is a distinction between drying the membrane before detection, by whatever means, and heating either a wet or dry membrane during detection. It is believed that if the membrane is not heated during detection, the main effect that is observed is one of drying, regardless of the drying method employed. Heating during detection provides the greatest enhancement effect.

It is readily appreciated that the drying and heating techniques disclosed herein are well understood according to those skilled in the art, and further that the listed techniques are intended to be merely representative and not exhaustive of all techniques available for purposes of the presently claimed process.

It also can be readily appreciated that the various drying and heating techniques disclosed herein may be optimized to suit a particular need of the researcher.

The enhanced chemiluminescent detection process of this invention is applicable to enzyme-based solid-phase assays which utilize 1,2-dioxetane substrates producing semi-stable intermediates. As the process is more specifically applied to well accepted chemiluminescent 1,2-dioxetane systems, reference is made to the disclosures of U.S. Pat. No. 4,931,223 and U.S. Pat. No. 4,952,707, both incorporated by reference herein. There are also numerous publications that describe the use of enzyme-triggered 1,2-dioxetanes for enzyme immunoassays (Bronstein et al., J. Biolumin. Chemilumin. 4, 99-111, 1989), Southern Blotting (Bronstein et al., BioTechniques 8, 310-314, 1990), and DNA sequencing (Tizard et al., Proc. Natl. Acad. Sci. 87, 4514-4518, 1990).

Such assays are based upon the use of specific binding interactions of one molecule by another. Specific binding partners include: antibody-antigen, complementary nucleic acid strands, binding protein-vitamin, and binding protein-nucleic acid. One member of the binding pair is disposed of and immobilized in some way on a solid support. The support is then incubated in a solution containing the second member of the binding pair, which is either directly labeled with an enzyme or which has attached a binding group, e.g., biotin or avidin, that can subsequently bind the enzyme label. In the latter case, the support is incubated in a solution containing the enzyme label. The support is then incubated in a solution containing the appropriate 1,2-dioxetane substrate for the enzyme label used. For example, 3-(2'-spiroadamantane)-4-methoxy-4-(3''-phosphoryloxy)-phenyl-1,2-dioxetane can be used when alkaline phosphatase is the enzyme label and 3-(2'-spiroadamantane)-4-methoxy-4-(3''-β-D-galactopyranosyloxyphenyl)-1,2-dioxetane can be used when β-D-galactosidase is the enzyme label. Some of the more common assays include enzyme-linked immunosorbent assays (ELISAs), DNA probe assays, and Southern Blotting.

The enzymatic reaction removes the enzyme-cleavable group from the 1,2-dioxetane, forming an anionic intermediate. The half-life of this intermediate is several hours when it is adsorbed onto a hydrophobic support, such as a nylon membrane. The intermediate decomposes by rupture of the dioxetane ring, forming two carbonyl compounds. At least one of these compounds is formed in an electronically excited state, which deactivates with the emission of radiant energy. An example of the reactions involved is as follows:

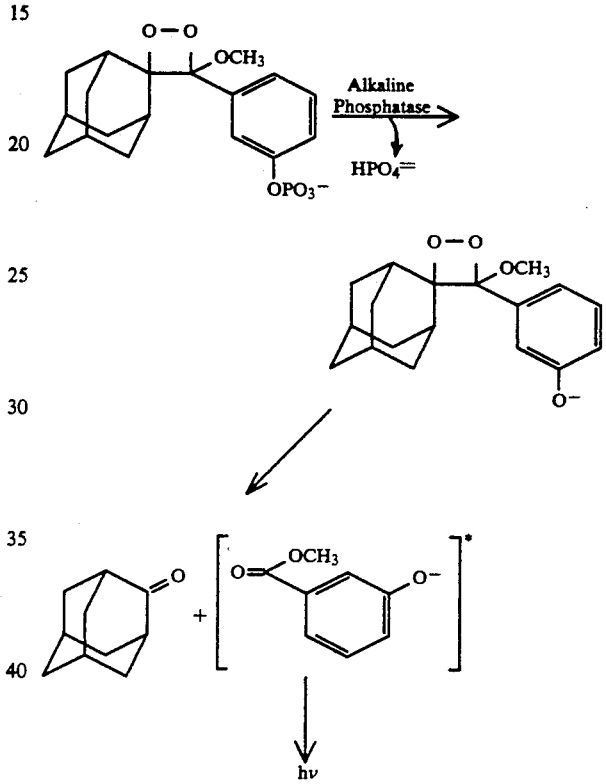

The drying and optional heating steps are carried out on the solid support after the incubation in substrate solution, and the chemiluminescent signal is measured, as described earlier. Heating the support provides an additional increase in the chemiluminescent signal, possibly by triggering the decomposition of the intermediate anion.

Preferred solid supports are hydrophobic and include, for example, nylon membranes, polymer beads, and microtiter plates and are used in the assay to separate bound from unbound enzyme label. The selection of solid support is a function of the type of assay being performed. Polymer beads and microtiter plates are typically used for immunoassays, although membranes can also be used. A membrane must be used in any assay that requires a transfer from an electrophoresis gel, i.e., Southern, Western, and Northern blots. The most commonly used solid supports are polymer beads, microtiter plates and membranes. However, the support can really be any shape, e.g., tubes and paddles. A hydrophobic support is preferred because it provides a hydrophobic environment which presumably stabilizes the anionic 1,2-dioxetane intermediate. It is theorized that with hydrophilic supports enhancement would be substantially less because the intermediate would decay more rapidly.

According to the invention, a complimentary binding partner of the substance is immobilized on a solid support. For example, if the target on the support is DNA, a complimentary DNA probe is used. For an immunoassay, an antibody-antigen pair is used. A second binding partner can be directly labeled with enzyme, or it can be modified to contain a second binding substance that will subsequently bind the enzyme label. In the present system, target DNA is immobilized on the membrane. The binding partner used is a complimentary DNA probe that has been modified to contain the vitamin biotin. After hybridization, in which the complimentary DNA strands anneal, an avidin-alkaline phosphatase conjugate is added. Avidin is a binding protein that has a strong affinity for biotin. Therefore, the complexation of biotin and avidin attaches the enzyme label to the DNA probe. Alkaline phosphatase is used when the 1,2-dioxetane is 3-(2'-spiroadamantane)-4-methoxy-4-(3''-phosphoryloxy) phenyl-1,2-dioxetane (commonly referred to as AMPPD). Additionally $\beta$-D-galactosidase is used when the 1,2-dioxetane is 3-(2'-spiroadamandane)-4-methoxy-4-(3''-$\beta$-D-galactopyranosyloxy-phenyl)- 1,2-dioxetane (commonly referred to as AMPGD).

The measurement of chemiluminescent signal intensity is performed by any of various techniques readily appreciated and understood by those skilled in the art. The methods vary as much as the purposes for which the present process may be used. Thus, detection enhancement may be useful for several applications including increasing the sensitivity in solid phase assays such as ELISAs and DNA probe assays. Other assays include Southern, Northern, and Western analyses. The enhancement process of this invention is useful for imaging nucleic acid or protein blots, in which case X-ray film is commonly employed. The primary advantage of the present enhancement process is that it greatly reduces the time required for the detection process, i.e., substrate incubation time plus detection of the chemiluminescent signal. A detection procedure that would take several hours can be done in 10 minutes or less. Other equipment, useful at the measurement stage include X-ray or photographic film and accompanying components, photomultiplier tubes, and electronic imaging detectors (such as charge-coupled device (CCD) cameras). Having the capability to capture the image quickly and at great intensity aviods other engineering problems such as camera cooling and background noise levels.

The invention will become more readily understood to the reader upon having reference to the following Examples herein:

EXAMPLES

General Procedures

The general enhancement process for drying the membrane prior to detection is as follows. The support is taken through the normal assay procedure depending on the type of assay being performed, e.g., ELISA, DNA probe assay, or Southern analysis. These procedures are well known in the art. In these assays, an enzyme label is attached to molecules immobilized on the solid support using an enzyme-labeled antibody, DNA probe, or an enzyme conjugated to biotin or avidin. The solid support is then incubated in a solution containing the for a period of time depending on the analyte concentration. Typical incubation times are from 5 to 30 minutes. The support is blotted dry on a piece of blotter paper and dried by placing in a convection oven for 5 to 10 minutes at 60° to 100° C. Alternatively, the support can be dried under vacuum for 15 to 30 minutes, or air-dried for 30 minutes followed by microwaving for 10 to 20 seconds. After drying, the chemiluminescent signal is measured with a suitable detector, e.g., photographic or X-ray film, photomultiplier tube or CCD camera. The integration time used for the detection varies depending on the detector used, the incubation time, and the analyte concentration. Typically, a 1 to 5 minutes exposure is used with X-ray film, and a 5 to 10 minutes exposure is used with a CCD camera.

The general enhancement process for heat-drying during signal detection is as follows. After immobilization of the enzyme-labeled molecule, the support is incubated in a solution containing the appropriate 1,2-dioxetane substrate for the enzyme label for a period of time depending on the analyte concentration. Typical incubation times are from 1 to 30 minutes. The support is blotted dry with a piece of blotter paper and placed on a heating element or in a heated chamber under the detector, e.g., photomultiplier tube or CCD camera. Alternatively, the support may be dried prior to signal collection. In either case, the support is heated during signal integration. The temperature for the heating process is between 40 to 100° C. The support is heated for 0 to 10 minutes before the signal is measured. This is usually done by taking a series of measurements, and selecting the one that gives the best signal to background ratio. The integration time varies depending on the analyte concentration, heating temperature, and incubation time. Typical integration times are from 30 seconds to 5 minutes.

EXAMPLE 1

Enhanced Chemiluminescent Detection of Biotinylated DNA on a Nylon Membrane Using CCD Camera Dilutions of a biotinylated lambda DNA solution (Vector Laboratories) were made in 6X SSC buffer (0.9 M sodium chloride and 0.09 M tri-sodium citrate), containing sheared calf thymus DNA (5 ng/uL), to give a range of concentrations, i.e., 50, 40, 30, 20, 10, 5 and 1 pg/200 uL. The solutions were slot-blotted onto an uncharged nylon membrane (MSI) by applying 200 uL of the diluted solutions to the wells of a slot-blot apparatus (Bio-Rad, Bio-Dot SF). The wells were washed several times with 6X SSC buffer. The membrane was dried under a heat lamp for 5 minutes and UV-crosslinked for 2 minutes using a Fotodyne UV 450 Transilluminator.

The membrane was incubated in I-Lightr TM blocking buffer (Tropix), which contains 0.2% I-Light in phosphate-buffered saline (PBS), for 30 minutes. The membrane was then placed in a solution containing avidin-alkaline phosphatase conjugate (Avidx TM, Tropix) in I-Light blocking buffer (5 uL per 20 ml) for 30 minutes After this time, the membrane was washed twice with I-Light blocking buffer for 5 minutes each, followed by four-5 minute washes with a solution of 0.3% Tween 20 in PBS. The membrane was washed four more times in assay buffer (0.05 M, pH 9.5 carbonate buffer containing 1 mM magnesium chloride).

The membrane was incubated in 0.25 mM AMPPD ™ (Tropix) substrate solution, prepared in assay buffer, for 15 minutes. The membrane was removed from the substrate solution, blotted on a piece of blotter paper to remove excess solution, and placed on an electrically heated block at 70° C. under a Charge Coupled Device camera (Star 1, Photometrics LTD.). A series of 2 minute exposures was taken immediately so that the signal was captured during the heating process. The intensity of the bands on the image of the second exposure was quantified using computer analysis. The results are given in Table 1.

TABLE 1

Chemiluminescent Intensities of Biotinylated DNA on a Nylon Membrane Using Enhanced Detection with CCD Camera

| DNA Load (pg) | Intensity (arbitrary light units) |
|---|---|
| 30 | 88.4 |
| 20 | 74.9 |
| 10 | 37.2 |

COMPARATIVE EXAMPLE 1

Normal Chemiluminescent Detection of Biotinylated DNA on a Nylon Membrane Using CCD Camera A slot-blotted membrane was prepared and treated as described in Example 1. After incubation in AMPPD substrate solution for 15 minutes, the membrane was sealed in a plastic bag and incubated for 15 more minutes. The bag was placed under the CCD camera and a 5 minute exposure was taken. The intensity of the bands was quantified as described in Example 1. The results of these controls taken over the course of several days are shown in Table 2.

TABLE 2

Normal Chemiluminescent Detection of Biotinylated DNA on a Nylon Membrane Using Normal Detection With CCD Camera

| DNA Load (pg) | Intensity (arbitrary light units) |
|---|---|
| 40 | 0.755 |
| 30 | 0.558 |
| 20 | 0.331 |
| 10 | Not detectable |

As can be seen by comparing the results in Tables 1 and 2, the enhanced procedure using heat-drying during detection provides up to a 100 fold increase in intensity with much shorter incubation and exposure times. Enhanced detection was done using a 15 minute incubation in substrate and a 2 minute exposure, while a 30 minute substrate incubation and a 5 minute exposure were used for the normal detection.

EXAMPLE 2

Enhanced Chemiluminescent Detection of Biotinylated DNA on a Nylon Membrane Using X-Ray Film A slot-blotted membrane was prepared and treated as described in Example 1. After incubation in AMPPD substrate solution for 5 minutes, the membrane was blotted dry on a piece of blotter paper, taped to a fresh piece of blotter paper, and dried in a hybridization oven at 60° C. for 5 minutes. The membrane was removed from the oven and exposed to X-ray film (Kodak XAR) for 5 minutes. The film image was transferred to a computer for analysis using a Cohu camera. The results are shown in Table 3.

TABLE 3

Chemiluminescent Intensities of Biotinylated DNA on a Nylon Membrane Using Enhanced Detection with X-Ray Film

| DNA Load (pg) | Intensity (arbitrary light units) |
|---|---|
| 50 | 2.016 |
| 40 | 1.259 |
| 30 | 0.810 |
| 20 | 0.490 |

COMPARATIVE EXAMPLE 2

Normal Chemiluminescent Detection of Biotinylated DNA on a Nylon Membrane Using X-Ray Film A slot-blotted membrane was prepared and treated as described in Example 1. After incubation in AMPPD substrate solution for 15 minutes, the membrane was sealed in a plastic bas and exposed to X-ray film (Kodak XAR) for 15 minutes. The film image was transferred to a computer for analysis using a Cohu camera. The results are shown in Table 4.

TABLE 4

Chemiluminescent Intensities of Biotinylated DNA on a Nylon Membrane Using Normal Detection with X-Ray Film

| DNA Load (pg) | Intensity (arbitrary light units) |
|---|---|
| 50 | 1.144 |
| 40 | 0.943 |
| 30 | 0.476 |
| 20 | 0.278 |

As can be seen by comparing the results in Tables 3 and 4, the enhanced detection, using oven drying of the membrane before exposure to film, gives signals that are approximately 70% higher than the normal detection. Both the substrate incubation time and the exposure time were much shorter with the enhanced detection. The total time for enhanced detection was one-half that used in the normal detection.

EXAMPLE 3

Enhanced Chemiluminescent Detection of Biotinylated DNA Using Heat Lamp-Drying Prior to Detection with a CCD Camera A slot-slotted membrane was prepared and treated as described in Example 1. After incubation in AMPPD substrate solution for 15 minutes, the membrane was placed on a sheet of blotter paper and dried under a lamp (Thermajust ® Infra-Red Heater) for 15 minutes. A setting of 9 was used on the lamp, which had a 375 watt bulb. The lamp was positioned approximately 8.5 inches from the membrane. The dried membrane was then placed under the CCD camera and a 5 minute exposure was taken. The intensity of the bands was quantified as described in Example 1. The results are shown in Table 5.

TABLE 5

Chemiluminescent Intensities of Biotinylated DNA on a Nylon Membrane Using Heat Lamp-Drying Prior to CCD Camera Detection

| DNA Load (pg) | Intensity (arbitrary light units)* |
|---|---|
| 40 | 2.53 |
| 30 | 1.91 |
| 20 | 1.23 |
| 10 | 0.650 |

The enhanced effect can be seen by comparing these intensities with those shown in Table 2 for Comparative Example 1.

EXAMPLE 4

Enhanced Chemiluminescent Detection of Biotinylated DNA Using Vacuum Drying Prior to Heating During Detection with a CCD Camera A slot-blotted membrane was prepared and treated as described in Example 1. After incubation in AMPPD substrate solution for 15 minutes, the membrane was dried in a vacuum desiccator for 15 minutes. The dried membrane was then placed on an electrically heated block at 75° C. under the CCD camera and a 2 minute exposure was taken. The intensity of the bands was quantified as described in Example 1. The results are shown in Table 6.

TABLE 6

Chemiluminescent Intensities of Biotinylated DNA on a Nylon Membrane Using Vacuum Drying Prior to Heating During CCD Camera Detection

| DNA Load (pg) | Intensity (arbitrary light units) |
| --- | --- |
| 40 | 66.3 |
| 30 | 56.1 |
| 20 | 41.0 |
| 10 | 22.8 |

The enhanced effect can be seen by comparing these intensities with those shown in Table 2.

EXAMPLE 5

Enhanced Chemiluminescent Detection of Biotinylated DNA Using Air-Drying Followed by Microwave Heating Prior to Detection with a CCD Camera A slot-blotted membrane was prepared and treated as described in Example 1. After incubation in AMPPD substrate solution for 15 minutes, the membrane was placed on a sheet of blotter paper and air-dried for 10 minutes. The membrane was then placed into a commercial 750 watt microwave oven for two consecutive 10 second intervals at the full power setting. The membrane was then placed under the CCD camera and a 5 minute exposure was taken. The intensity of the bands was quantified as described in Example 1. The results are shown in Table 7.

TABLE 7

Chemiluminescent Intensities of Biotinylated DNA on a Nylon Membrane Using Air-Drying and Microwave Heating Prior to Detection with a CCD Camera

| DNA Load (pg) | Intensity (arbitrary light units) |
| --- | --- |
| 40 | 3.16 |
| 30 | 2.66 |
| 20 | 2.26 |
| 10 | 1.46 |

The enhanced effect can be seen by comparing these intensities with those shown in Table 2.

EXAMPLE 6

Enhanced Chemiluminescent Detection of Biotinylated DNA Using Vacuum Drying Prior to Detection with a CCD Camera A slot-blotted membrane was prepared and treated as described in Example 1. After incubation in AMPPD substrate solution for 15 minutes, the membrane was placed on a sheet of blotter paper and dried in a vacuum desiccator for 15 minutes. The membrane was then placed under the CCD camera and a 5 minute exposure was taken. The intensity of the bands was quantified as described in Example 1. The results are shown in Table 8.

TABLE 8

Chemiluminescent Intensities of Biotinylated DNA on a Nylon Membrane Using Vacuum Drying Prior to Detection with a CCD Camera

| DNA Load (pg) | Intensity (arbitrary light units) |
| --- | --- |
| 40 | 1.82 |
| 30 | 1.71 |
| 20 | 1.06 |
| 10 | 0.695 |

The enhanced effect can be seen by comparing these intensities with those shown in Table 2.

EXAMPLE 7

Figure 2:
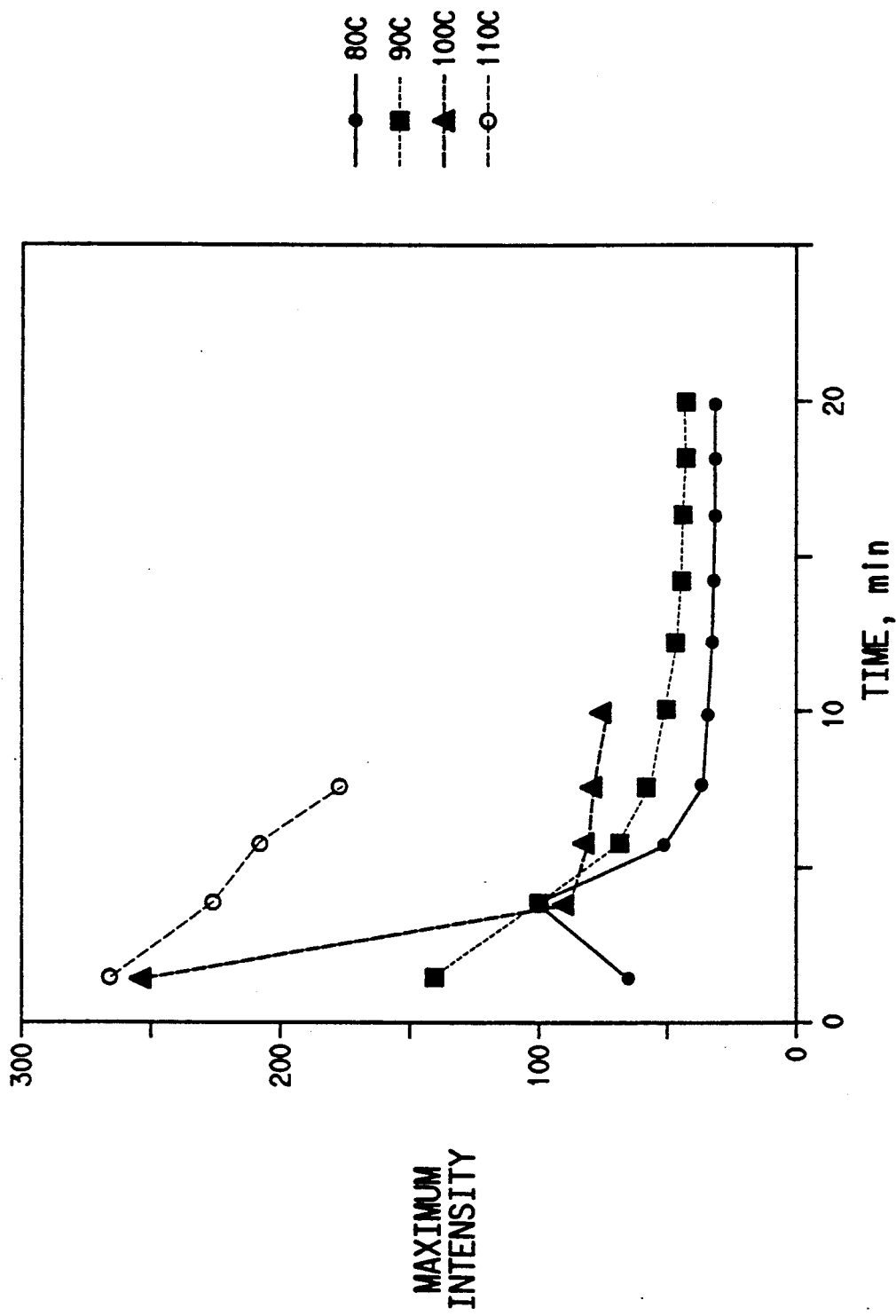

Effect of Temperature on Chemiluminescent Signal for Wet Membranes Heat-Dried During Detection with a CCD Camera Slot-blotted membranes were prepared and treated as described in Example 1. The membranes were incubated in AMPPD substrate solution for 5 minutes. A membrane was placed on an electrically-heated plate, kept at a preselected temperature, under a CCD camera and a series of 2 minute exposures were taken. This procedure was repeated with other membranes using different uses ranging from 24°–110° C. The maximum chemiluminescent signal obtained as a function of time at each temperature is shown in FIGS. 1 and 2.

EXAMPLE 3

Effect of Heating Wet Membranes on Chemiluminescent Signal

Biotinylated lambda DNA solutions were prepared by diluting the stock solution (Vector Laboratories, 50 ng/uL) with an aqueous solution containing 0.02% bromphenol blue, 0.02% xylene cyanol, 2.1% ficoll in 8.0 mM EDTA. The dilutions used were 1:200, 1:400, 1:800, and 1:1600. The solutions were heated for 10 minutes at 5° C. and loaded into a 0.8% agarose gel (10 uL per well) in a Bio-Rad Mini-Sub Cell. Duplicate loadings of each dilution were made so that both halves of the gel were identical. The unit was filled with pH 8.65 TTNE buffer (20 mM tricine, 50 mM Tris buffer, 5 mM sodium acetate and 10 mM EDTA). The elctrophoretic separation was carried out for 1 hour at 80 volts.

The DNA was transferred to a nylon membrane (MSI) using a Hoefer Mighty Small Transphor ™ Electroblot unit (TE 22), which was kept at 4° C. using a refrigerated circulating bath. The transfer was done for 20 minutes at 40 volts and another 20 minutes at 50 volts using TTNE buffer. The membranes were dried for 5 minutes using a heat lamp and UV-crosslinked for 2 minutes, as described in Example 1. The membranes were then cut in half for use in the study.

The membranes were incubated in I-Light blocking buffer for 20 minutes replacing the solution every 5 minutes The membranes were then incubated in Avidx ™ avidin-alkaline phosphatase conjugate for 30 minutes, and were washed as described in Example 1.

The membrane halves were incubated in 0.2 mM AMPPD substrate solution for 5 minutes and then sealed into a plastic bag. After 7 more minutes the membranes were exposed to X-ray film for 12 minutes. The signal obtained from all membrane halves was comparable. After another 12 minutes, the membranes were treated as follows: one membrane half was left sealed in the bag (control), one membrane half was removed from the bag and dried under a heat lamp while on top of the bag, one membrane was placed under the heat lamp while still in the bag to keep it wet during the heating process, other membrane halves were kept sealed bags and placed in water baths at 37°, 60°, or 75° C. for 10 minutes.

All the treated membrane halves were exposed to X-ray film again for a 12 minute exposure. The following results were obtained. The membrane that was heat-dried under the heat lamp had a greater signal than the control. The membrane that was heated to 37° C. while wet had a signal similar to that of the control. The membrane that was heated to 60° C. while wet had a lower signal than the control. Both the membrane that was heated under the heat lamp while wet and the membrane that was heated at 75° C. while wet had no detectable signal. This study shows that heating membranes while they are wet gives no significant improvement in signal or a decrease in signal depending on the temperature.

What is claimed is:

1. A process for the enhancement of the chemiluminescent signal intensity of an enzyme-triggerable 1,2-dioxetane, wherein the 1,2-dioxethane are a substrate for said enzyme, comprising:
    (a) providing a solid hydrophobic support having enzyme disposed thereon and treating the support with a solution including 1,2-dioxetanes to enzyme-trigger the 1,2-dioxetanes to produce a semi-stable intermediate decomposable to a chemiluminescent product adsorbed on said support;
    (b) drying said solid support and said intermediate thereon;
    (c) optionally heating said solid support and said intermediate thereon simultaneously with drying or thereafter; and
    (d) detecting the enhanced chemiluminescence;
    and further that drying with or without heating is conducted either prior to or simultaneously with detection.

2. The process of claim 1 wherein drying alone is conducted prior to detection.

3. The process of claim 1 wherein drying alone is conducted prior to detection and heating is conducted simultaneously with detection.

4. The process of claim 1 wherein drying and heating are conducted prior to detection.

5. The process of claim 1 wherein drying alone is conducted simultaneously with detection.

6. The process of claim 1 wherein drying and heating are conducted simultaneously with detection.

7. The process of claim 1 wherein drying is accomplished by subjecting the solid support for a suitable time and temperature to a procedure selected from the group consisting of vacuum drying, convection drying, air drying, the use of microwave energy, and the use of electrical energy.

8. The process of claim 7 wherein vacuum drying is applied for 15 to 30 minutes at ambient temperature.

9. The process of claim 7 wherein convection drying is applied in a convection oven for 5-30 minutes at 30°-100° C.

10. The process of claim 7 wherein air drying is conducted for at least 30 minutes at ambient temperature.

11. The process of claim 1 wherein heating is accomplished by introducing the solid support for a time and temperature suitable to enhance chemiluminescence to a selected level of emission to a procedure selected from the group consisting of electrical heating, infrared radiation heating, convective heating, and microwave heating.

12. The process of claim 11 wherein heating is conducted for 1-10 minutes at 40°-100° C.

13. A method for the detection of a target molecule in a solid-phase assay utilizing a chemiluminescent enzyme-triggerable 1,2-dioxetane comprising:
    (a) providing a solid support having one member of a specific binding pair disposed thereon wherein the member of the specific binding pair is the target molecule or is able to capture the target molecule from the sample solution;
    (b) adding a solution containing the complimentary binding partner which is either directly conjugated to an enzyme label or which can subsequently bind a second binding partner which is conjugated to an enzyme label;
    (c) optionally incubating said solid support in a solution containing said second binding partner that is conjugated to an enzyme label;
    (d) incubating the solid support including the specific binding pair or pairs and the enzyme label in a solution containing an enzyme-triggerable 1,2-dioxetane wherein the 1,2-dioxetane is a substrate for said enzyme to produce a semi-stable intermediate decomposable to a chemiluminescent product adsorbed on said support;
    (e) drying said solid-support and said intermediate thereon;
    (f) optionally heating said solid support and said intermediate thereon simultaneously with drying or thereafter to enhance the intensity of the chemiluminescent signal; and
    (g) detecting the enhanced chemiluminescence; and further that drying with or without heating is conducted either prior to or simultaneously with detection.

14. The process of claim 13 wherein said solid support is hydrophobic and selected from the group consisting of nylon membranes, polymer beads, and microtiter plates.

15. The process of claim 13 wherein said specific binding pairs are selected from the group consisting of complimentary nucleic acid strands, antibody-antigen, binding protein-vitamin, and binding protein-nucleic acid.

16. The process of claim 13 wherein said 1,2-dioxetane is 3-(2'-spiroadamantane)-4-methoxy-4-(3''-phosphorlyoxy) phenyl-1,2-dioxetane and said second binding partner is an alkaline phosphatase conjugate, or said 1,2-dioxetane is 3-(2'-spriroadamantane)-4-methoxy-4-(3''-$\beta$-D-galactopyranosyloxy-phenyl)-1,2-dioxetane and said second binding partner is a $\beta$-D-galactosidase conjugate.

17. The process of claim 13 wherein the chemiluminescent signal intensity is detected using equipment selected from the group consisting of X-ray or photographic film, a photomultiplier tube, or an electronic imaging detector.

18. The process of claim 13 wherein the assay is selected from the group consisting of ELISA (enzyme-Linked Immunosorbent Assay), DNA probe assay, and Southern, Northern and Western analyses.

* * * * *